United States Patent
Pugh

(10) Patent No.: US 7,992,523 B1
(45) Date of Patent: Aug. 9, 2011

(54) RADIOGRAPHY IMAGING SYSTEM

(75) Inventor: Brian T. Pugh, St. Cloud, FL (US)

(73) Assignee: Brian Pugh, Saint Cloud, FL (US)

( * ) Notice: Subject to any disclaimer, the term of this patent is extended or adjusted under 35 U.S.C. 154(b) by 143 days.

(21) Appl. No.: 12/584,907

(22) Filed: Sep. 15, 2009

(51) Int. Cl.
*A01K 29/00* (2006.01)

(52) U.S. Cl. ........................................ 119/751; 119/417

(58) Field of Classification Search .................. 119/751, 119/417, 416, 418, 712, 752–756, 814; 378/208; 600/415, 410, 411; 5/601; 604/523
See application file for complete search history.

(56) References Cited

U.S. PATENT DOCUMENTS

| | | | | |
|---|---|---|---|---|
| 2,027,318 | A * | 1/1936 | Nelson | 378/209 |
| 2,705,475 | A * | 4/1955 | Johnisee | 119/753 |
| 3,286,693 | A * | 11/1966 | Clarke, Jr. et al. | 119/712 |
| 3,474,763 | A * | 10/1969 | Kissil et al. | 119/751 |
| 3,739,751 | A * | 6/1973 | Mohr et al. | 119/751 |
| 4,269,149 | A * | 5/1981 | Thomas | 119/729 |
| 5,099,792 | A * | 3/1992 | Cannon et al. | 119/420 |
| 5,167,160 | A * | 12/1992 | Hall, II | 73/864.91 |
| 5,320,069 | A * | 6/1994 | Anderson et al. | 119/751 |
| 5,927,234 | A * | 7/1999 | Siegel | 119/751 |
| 6,651,587 | B1 * | 11/2003 | DeFord et al. | 119/420 |
| 7,865,226 | B2 * | 1/2011 | Chiodo | 600/407 |
| 2005/0056234 | A1 * | 3/2005 | Dazai et al. | 119/757 |
| 2008/0168951 | A1 * | 7/2008 | Starr et al. | 119/751 |
| 2009/0000567 | A1 * | 1/2009 | Hadjioannou et al. | 119/755 |
| 2009/0245474 | A1 * | 10/2009 | Chiodo | 378/208 |
| 2010/0100072 | A1 * | 4/2010 | Chiodo | 604/523 |
| 2010/0269260 | A1 * | 10/2010 | Lanz et al. | 5/601 |

OTHER PUBLICATIONS

"Nose Cone Animal Holders", found in online catalog, Kent Scientific Corporation, 2006-2009, http://www.kentscientific.com/products/productView.asp?ProductId=6244.
www.Kentscientific.com catalogue, pp. 2,14, 46 with photographs of "rat holder," "tube rodent holders," and "animal holders".

* cited by examiner

*Primary Examiner* — T. Nguyen
(74) *Attorney, Agent, or Firm* — Michael Colitz, Jr.

(57) ABSTRACT

An outer capsule terminates in a closed bottom section. An upper section is formed with an open threaded top. The top has a removable cap. An inner capsule has a lower section and an open upper section. The lower section terminates in an open bottom. An aperture is provided in the closed bottom section of the outer capsule for the passage of a lower most extent of the inner capsule and the securement there between. The capsules are fabricated of a transparent material. A bevel extends through the lower section of the outer capsule. A hose couples the bevel and the inner capsule. A wad of cotton is provided in the lower open end of the capsule.

4 Claims, 3 Drawing Sheets

RADIOGRAPHY IMAGING SYSTEM

BACKGROUND OF THE INVENTION

1. Field of the Invention

The present invention relates to a radiography imaging system and more particularly pertains to decreasing the time required to perform radiography imagine in small test animals as used in veterinary medical practice while enhancing the quality of images produced.

2. Description of the Prior Art

The use of imaging systems of known designs and configurations is known in the prior art. More specifically, imaging systems of known designs and configurations previously devised and utilized for the purpose of aiding in radiography imagine through known methods and apparatuses are known to consist basically of familiar, expected, and obvious structural configurations, notwithstanding the myriad of designs encompassed by the crowded prior art which has been developed for the fulfillment of countless objectives and requirements.

Several examples of issued patents demonstrating the prior art will be indicated in the paragraphs to follow. Additionally, an Information Disclosure Statement enumerating several non-patented devices that were uncovered during our pre-filing patent search is being filed simultaneously with the filing of the present non-provisional utility patent application.

By way of example, U.S. Pat. No. 6,887,460 issued Apr. 12, 2005 to Ellis relates to an Animal Sorting and Grading System Using MRI to Predict Maximum Value. U.S. Pat. No. 6,852,392 issued Feb. 8, 2005 to Zan relates to a Small Animal Mount Assembly. Lastly, U.S. Pat. No. 4,934,320 issued Jun. 19, 1990 to Crespae relates to an Animal Restraining Device.

While these devices fulfill their respective, particular objectives and requirements, the aforementioned patents do not describe a radiography imaging system that allows for decreasing the time required to perform radiography imagine in small test animals as used in veterinary medical practice while enhancing the quality of images produced.

In this respect, the radiography imaging system according to the present invention substantially departs from the conventional concepts and designs of the prior art, and in doing so provides an apparatus primarily developed for the purpose of decreasing the time required to perform radiography imagine in small test animals as used in veterinary medical practice while enhancing the quality of images produced.

Therefore, it can be appreciated that there exists a continuing need for a new and improved radiography imaging system which can be used for decreasing the time required to perform radiography imagine in small test animals as used in veterinary medical practice while enhancing the quality of images produced. In this regard, the present invention substantially fulfills this need.

SUMMARY OF THE INVENTION

In view of the foregoing disadvantages inherent in the known types of imaging systems of known designs and configurations now present in the prior art, the present invention provides an improved radiography imaging system. As such, the general purpose of the present invention, which will be described subsequently in greater detail, is to provide a new and improved radiography imaging system and method which has all the advantages of the prior art and none of the disadvantages.

To attain this, the present invention essentially comprises a radiography imaging system. First provided is an outer capsule. The outer capsule has a cylindrical lower section. The lower section has an enlarged diameter. The enlarged diameter is provided over the majority of its length. The lower section terminates in a closed circular bottom. The outer capsule has a generally cylindrical upper section. The upper section has a reduced diameter. The upper section is formed with an open threaded top. The outer capsule has a generally conical intermediate section. The intermediate section is provided between the upper and lower sections.

A smaller inner capsule is provided. The small inner capsule has a cylindrical lower section. The lower section has an enlarged diameter. The enlarged diameter is provided over the majority of its length. The lower section terminates in an open circular bottom. The small inner capsule has a cylindrical open upper section. The upper section has a reduced diameter. The small inner capsule has a generally conical intermediate section. The intermediate section is provided between the upper and lower sections. The axial length of the smaller inner capsule is less than 50 percent of the length of the lower section of the outer capsule. An aperture is provided in the circular bottom. In this manner the lower most extent of the smaller capsule may pass through and be secured.

Provided next is a larger inner capsule. The large inner capsule has a cylindrical lower section. The lower section has an enlarged diameter. The enlarged diameter is provided over the majority of its length. The lower section terminates in an open circular bottom. The large inner capsule has a cylindrical open upper section. The upper section has a reduced diameter. The large inner capsule has a generally conical intermediate section. The intermediate section is provided between the upper and lower sections. The axial length of the larger inner capsule is greater than 50 percent of the length of the lower section of the outer capsule. An aperture is provided in the circular bottom. In this manner the lower most extent of the smaller capsule may pass through and be secured. All of the capsules are fabricated of a transparent plastic material.

A first bevel and a second bevel are provided next. The bevels extend through the lower section of the outer capsule in proximity to the intermediate section. A first clear airline hose is provided. The first clear airline hose couples the first bevel and the upper portion of the smaller inner capsule. A second clear airline hose is provided. The second clear airline hose couples the second bevel and the upper portion of the larger inner capsule. The bevels and the airline hoses are adapted to bring air into the inner capsules.

Further provided is a threaded cap. The cap is removably positioned on the threaded top of the outer capsule. In this manner a saline solution is adapted to be poured into the outer capsule and retained therein during use.

Provided last is a wad of cotton. The cotton is provided in the lower open end of each inner capsule. In this manner a small test animal in each inner capsule will stay still during a radiography imaging procedure. Also in this manner adequate airflow to each test animal is provided. Further in this manner, and, more importantly, signal strength for magnets of MRI when scanning such a small tissue mass, such as lab rodent subjects, is enhanced.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved radiography imaging system which has all of the advantages of the prior art imaging systems of known designs and configurations and none of the disadvantages.

It is another object of the present invention to provide a new and improved radiography imaging system which may be easily and efficiently manufactured and marketed.

It is further object of the present invention to provide a new and improved radiography imaging system which is of durable and reliable constructions.

An even further object of the present invention is to provide a new and improved radiography imaging system which is susceptible of a low cost of manufacture with regard to both materials and labor, and which accordingly is then susceptible of low prices of sale to the consuming public, thereby making such radiography imaging system economically available to the buying public.

Even still another object of the present invention is to provide a radiography imaging system for decreasing the time required to perform radiography imagine in small test animals as used in veterinary medical practice while enhancing the quality of images produced.

Lastly, it is an object of the present invention to provide a new and improved radiography imaging system. An outer capsule terminates in a closed bottom section. An upper section is formed with an open threaded top. The top has a removable cap. An inner capsule has a lower section and an open upper section. The lower section terminates in an open bottom. An aperture is provided in the closed bottom section of the outer capsule for the passage of a lower most extent of the inner capsule and the securement there between. The capsules are fabricated of a transparent material. A bevel extends through the lower section of the outer capsule. A hose couples the bevel and the inner capsule. A wad of cotton is provided in the lower open end of the capsule.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
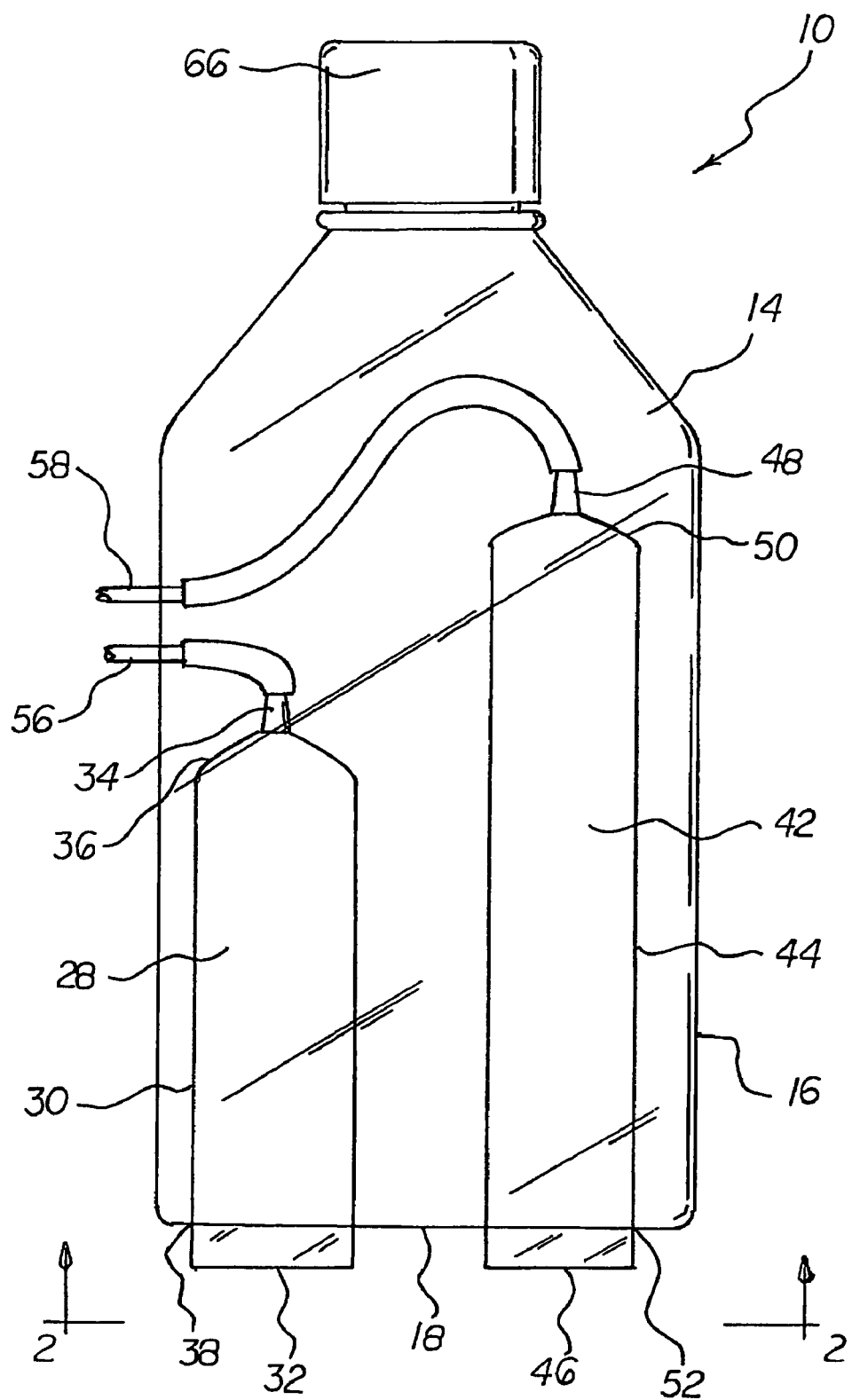
FIG. 1 is a front elevational view of a radiography imaging system constructed in accordance with the principles of the present invention.
Figure 2:
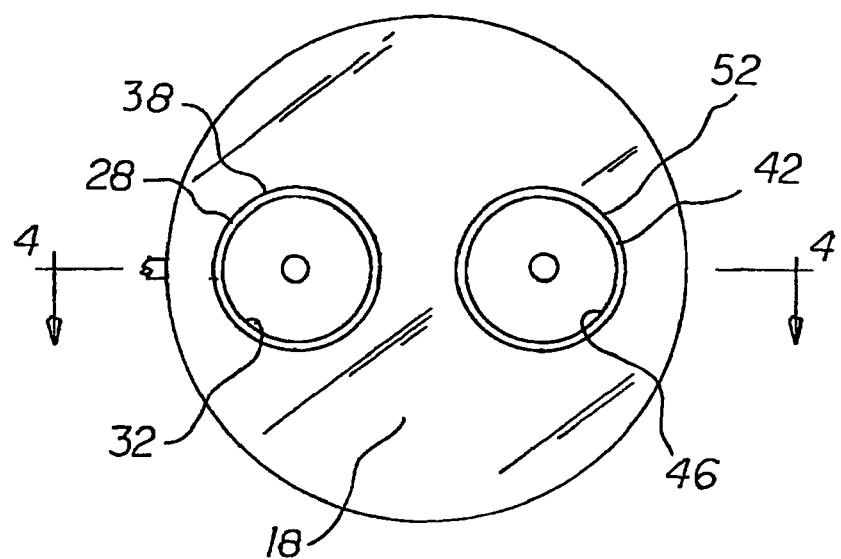
FIG. 2 is a bottom view of the system taken along line 2-2 of FIG. 1.
Figure 3:
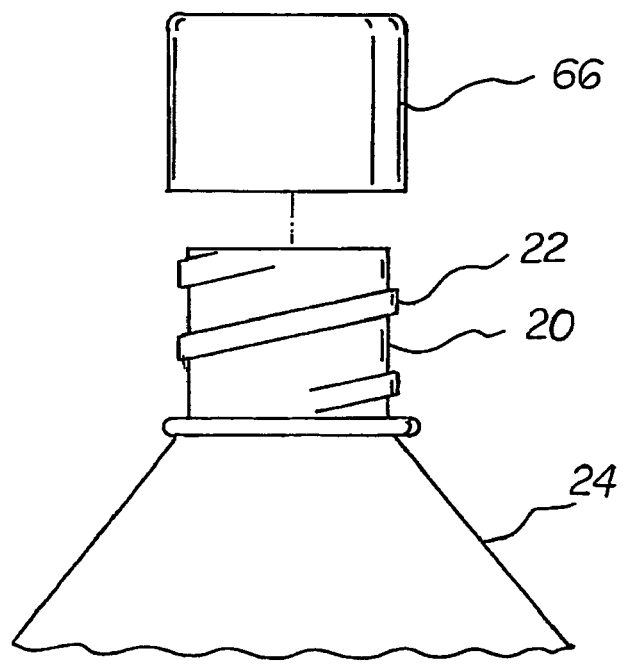
FIG. 3 is an explored perspective illustration of the top of the system shown in FIG. 1.
Figure 4:
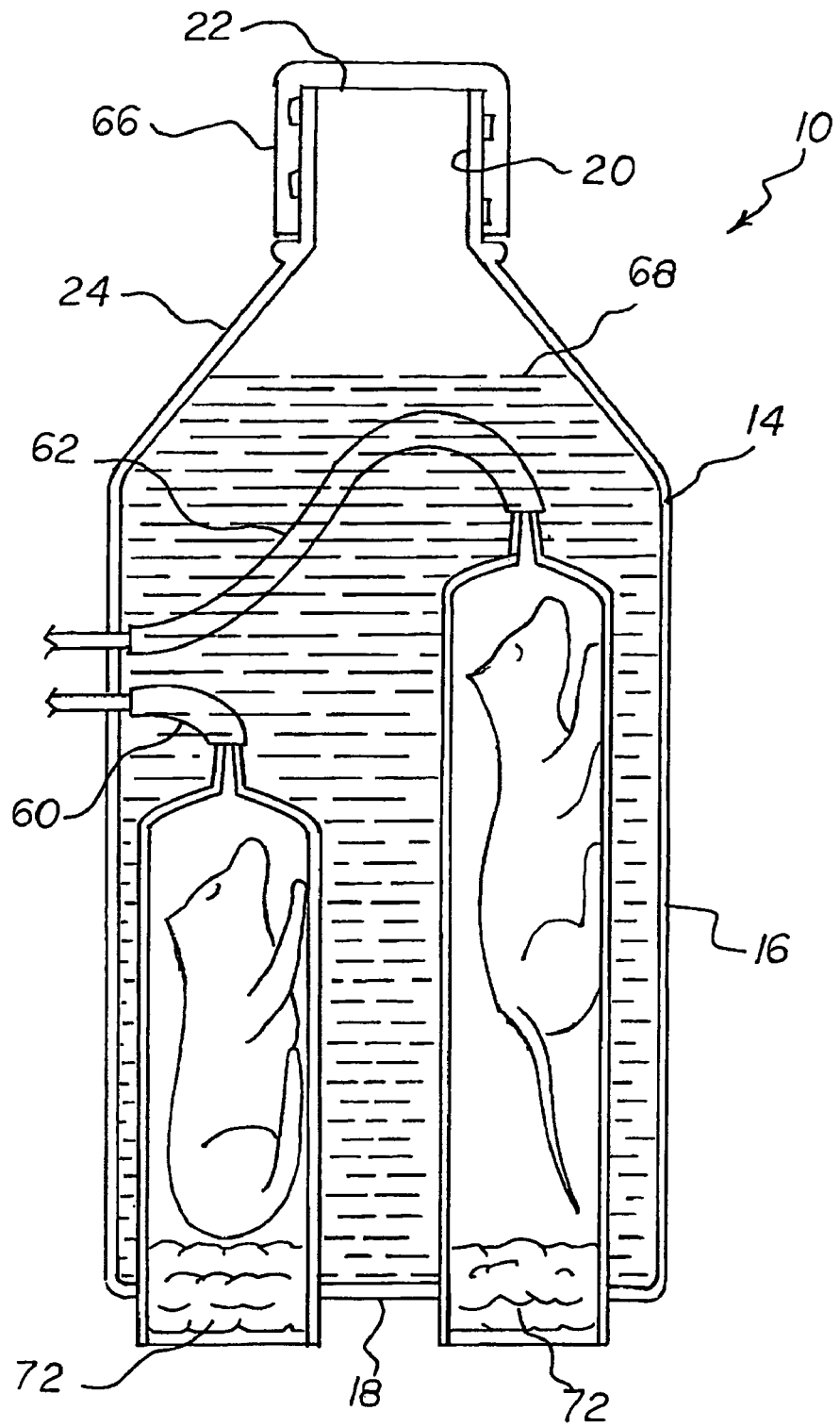
FIG. 4 is a cross sectional view taken along line 4-4 of FIG. 2.

With reference now to the drawings, and in particular to FIG. 1 thereof, the preferred embodiment of the new and improved radiography imaging system embodying the principles and concepts of the present invention and generally designated by the reference numeral 10 will be described.

The present invention, the radiography imaging system 10 is comprised of a plurality of components. Such components in their broadest context include an outer capsule, an inner capsule and a bevel. Such components are individually configured and correlated with respect to each other so as to attain the desired objective.

First provided is an outer capsule 14. The outer capsule has a cylindrical lower section 16. The lower section has an enlarged diameter. The enlarged diameter is provided over the majority of its length. The lower section terminates in a closed circular bottom 18. The outer capsule has a generally cylindrical upper section 20. The upper section has a reduced diameter. The upper section is formed with an open threaded top 22. The outer capsule has a generally conical intermediate section 24. The intermediate section is provided between the upper and lower sections.

A smaller inner capsule 28 is provided. The small inner capsule has a cylindrical lower section 30. The lower section has an enlarged diameter. The enlarged diameter is provided over the majority of its length. The lower section terminates in an open circular bottom 32. The small inner capsule has a cylindrical open upper section 34. The upper section has a reduced diameter. The small inner capsule has a generally conical intermediate section 36. The intermediate section is provided between the upper and lower sections. The axial length of the smaller inner capsule is less than 50 percent of the length of the lower section of the outer capsule. An aperture 38 is provided in the circular bottom. In this manner the lower most extent of the smaller capsule passes through the circular bottom of the outer capsule and is adhesively secured thereto.

Provided next is a larger inner capsule 42. The large inner capsule has a cylindrical lower section 44. The lower section has an enlarged diameter. The enlarged diameter is provided over the majority of its length. The lower section terminates in an open circular bottom 46. The large inner capsule has a cylindrical open upper section 48. The upper section has a reduced diameter. The large inner capsule has a generally conical intermediate section 50. The intermediate section is provided between the upper and lower sections. The axial length of the larger inner capsule is greater than 50 percent of the length of the lower section of the outer capsule. An aperture 52 is provided in the circular bottom. In this manner the lower most extent of the larger capsule passes through the circular bottom of the outer capsule and is adhesively secured thereto. All of the capsules are fabricated of a transparent plastic material.

A first bevel 56 and a second bevel 58 are provided next. The bevels extend through the lower section of the outer capsule in proximity to the intermediate section. A first clear airline hose 60 is provided. The first clear airline hose couples the first bevel and the upper portion of the smaller inner capsule. A second clear airline hose 62 is provided. The second clear airline hose couples the second bevel and the upper portion of the larger inner capsule. The bevels and the airline hoses are adapted to bring air into the inner capsules.

Further provided is a threaded cap 66. The cap is removably positioned on the threaded top of the outer capsule. In this manner a saline solution 68 is adapted to be poured into the outer capsule and retained therein during use.

Provided last is a wad of cotton 72. The cotton is provided in the lower open end of each inner capsule. In this manner a small test animal in each inner capsule will stay still during a radiography imaging procedure. Also in this manner adequate airflow to each test animal is provided. Further in this manner, and, more importantly, signal strength for magnets of MRI when scanning such a small tissue mass, such as lab rodent subjects, is enhanced.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A radiography imaging system comprising:
    an outer capsule terminating in a closed bottom section and an upper section formed with an open threaded top with a removable cap;
    an inner capsule having a lower section terminating in an open bottom and an open upper section, an aperture in the closed bottom section of the outer capsule for the passage of the lower section of the inner capsule and the securement there between, the capsules being fabricated of a transparent material;
    a bevel extending through the lower section of the outer capsule with a hose coupling the bevel and the inner capsule; and
    a wad of cotton in the open bottom of the inner capsule.

2. The system as set forth in claim 1 wherein the inner capsule includes a smaller inner capsule and a larger inner capsule, each inner capsule having a cylindrical lower section of an enlarged diameter over the majority of its length terminating in an open circular bottom and a cylindrical open upper section of a reduced diameter and with a generally conical intermediate section between the upper and lower sections, and with apertures in the circular bottom of the outer capsule for the passage of the lower most extent of the smaller capsules and the securement there between, all of the capsules being fabricated of a transparent plastic material.

3. The system as set forth in claim 2 wherein the bevel and hose include a first and a second bevel extending through the lower section of the outer capsule with a first clear airline hose coupling the first bevel and the upper portion of the smaller inner capsule and with a second clear airline hose coupling the second bevel and the upper portion of the larger inner capsule, the bevels and the airline hoses adapted to bring air into the inner capsules.

4. A radiography imaging system for decreasing the time required to perform radiography imaging in small test animals as used in veterinary medical practice while enhancing the quality of images produced comprising, in combination:
    an outer capsule having a cylindrical lower section of an enlarged diameter over the majority of its length terminating in a closed circular bottom with a bottom aperture and a generally cylindrical upper section of a reduced diameter formed with an open threaded top and with a generally conical intermediate section between the upper and lower sections;
    a smaller inner capsule having a cylindrical lower section of an enlarged diameter over the majority of its length terminating in an open circular bottom and a cylindrical open upper section of a reduced diameter and with a generally conical intermediate section between the upper and lower sections, the axial length of the smaller inner capsule being less than the length of the lower section of the outer capsule with the bottom aperture in the circular bottom of the outer capsule for the passage of the smaller inner capsule and the securement there between;
    a larger inner capsule having a cylindrical lower section of an enlarged diameter over the majority of its length terminating in an open circular bottom and a cylindrical open upper section of a reduced diameter and with a generally conical intermediate section between the upper and lower sections, the axial length of the larger inner capsule being greater than the length of the lower section of the outer capsule with the bottom aperture in the circular bottom of the outer capsule for the passage of the larger inner capsule and the securement there between, all of the capsules being fabricated of a transparent plastic material;
    a first bevel and a second bevel extending through the lower section of the outer capsule in proximity to the intermediate section with a first clear airline hose coupling the first bevel and the upper portion of the smaller inner capsule and with a second clear airline hose coupling the second bevel and the upper portion of the larger inner capsule, the bevels and the airline hoses adapted to bring air into the inner capsules;
    a threaded cap removably positioned on the threaded top of the outer capsule whereby a saline solution is adapted to be poured into the outer capsule and retained therein during use; and
    a wad of cotton in the lower open end of each inner capsule to insure that a small test animal in each inner capsule stays still during a radiography imaging procedure, to provide adequate airflow to each test animal and, more importantly, to enhance the signal strength for magnets of MRI when scanning such a small tissue mass such as lab rodent subjects.

\* \* \* \* \*